United States Patent [19]

Haney et al.

[11] Patent Number: 4,813,944
[45] Date of Patent: Mar. 21, 1989

[54] MULTIPURPOSE DISPOSABLE ABSORBENT PAD

[75] Inventors: Glen K. Haney, 110 Wynnmeade Pkwy., Peachtree City, Ga. 30269; Victor Kramer, Atlanta, Ga.

[73] Assignee: Glen Kyle Haney, Jonesboro, Ga.

[21] Appl. No.: 144,128

[22] Filed: Jan. 5, 1988

[51] Int. Cl.[4] .............................................. A61F 13/16
[52] U.S. Cl. ........................................ 604/358; 5/484
[58] Field of Search .................. 604/370, 358, 369; 5/484

[56] References Cited

U.S. PATENT DOCUMENTS

| | | | |
|---|---|---|---|
| 3,110,312 | 11/1963 | Wirth | 604/369 |
| 3,208,451 | 9/1965 | Porter et al. | 604/370 |
| 3,306,966 | 2/1967 | Matejcek et al. | 604/369 |
| 3,308,826 | 3/1967 | Blake | 604/370 |
| 3,315,676 | 4/1967 | Cooper | 604/370 |
| 3,322,594 | 5/1967 | Lucas et al. | 604/370 |
| 3,375,827 | 3/1968 | Bletzinger et al. | 604/369 |
| 3,431,911 | 3/1969 | Meisel, Jr. | 604/360 |
| 3,468,311 | 8/1969 | Gallagher | 604/369 |
| 3,576,039 | 3/1971 | Roberts | 5/484 |
| 3,974,308 | 8/1976 | Winters | 5/484 |
| 4,021,870 | 5/1977 | Walters | 5/484 |
| 4,173,046 | 11/1979 | Gallagher | 604/370 |
| 4,499,131 | 2/1985 | Knox | 5/484 |
| 4,524,474 | 6/1985 | Svensson | 5/484 |
| 4,536,433 | 8/1985 | Sagi et al. | 604/358 |
| 4,627,122 | 12/1986 | Hopp | 5/484 |

Primary Examiner—John D. Yasko
Attorney, Agent, or Firm—David P. Kelley

[57] ABSTRACT

A disposable multi-purpose absorbent pad has a top layer of adsorbent material, a second layer of absorbent material, and a third layer of liquid impermeable material, the layers being joined at the edges of the pad forming a peripheral seal. The underside of the third layer is coated with a foam material covering the area within the peripheral seal.

6 Claims, 1 Drawing Sheet

MULTIPURPOSE DISPOSABLE ABSORBENT PAD

BACKGROUND OF THE INVENTION

This invention relates to disposable absorbent pads and, more particularly, to pads for preventing the spread of, and collecting, potentially harmful or unsanitary liquids in a variety of situations.

In, for example, the toilet areas of athletic facility dressing rooms, it is common for the users thereof to walk about in their bare feet. Thus it often happens that one may use a urinal while standing barefoot in an area that has been contaminated by prior careless users paying scant attention to what they are doing. Urine or other liquids splashing on the floor can contaminate a large area under and adjacent the urinal. If the user has any sort of lesions on his feet, such as may be caused by athletes foot, the consequences may be quite serious, such as contracting Aids or other dangerous diseases.

Various arrangements for protecting users by keeping an area at least partly sanitary are shown in the prior art. One such is shown in U.S. Pat. No. 4,328,275 of Vargo. The Vargo device is a floor mat for absorbing liquid spills while permitting the user to stand on the mat. This is achieved by a plurality of projections having a liquid repellant coating which support the user. Such an arrangement does not achieve complete sanitation, however, since the liquid does strike the projections and some necessarily remains thereon, presenting a potential risk to the user.

Another sanitary pad arrangement for use in toilet areas is shown in U.S. Pat. No. 4,125,656 of Creamer. The pad of Creamer is an absorbent pad having a waterproof backing and configured to fit closely around the base of a toilet. The pad may be held in place as by gluing to the floor.

In the various arrangements for use on floors or similar surfaces, the problem of slippage of the pad is not addressed, other than the Creamer solution of gluing to the floor. Thus even where the pad absorbs moisture successfully, the area of use is, by its nature, inherently damp, and most absorbent pads being provided with a moisture impervious backing, eventually tend to slip out of position.

Moisture absorbent pads are also used in beds or wheelchairs to absorb fluids from incontinent patients, for example, most of which are aimed at presenting a relatively dry surface for the patient's comfort. One such pad is shown in U.S. Pat. No. 4,173,046 of Gallagher which comprises an underlying liquid impervious layer, an absorptive layer, a perforated liquid impervious layer, and a top layer of hydrophobic closed cell foam material having a plurality of large openings therein to permit passage of liquid to the underlying layers. Such material as used to form the top layer will, by its nature, fail to remove all liquid since some of it will simply remain on the top surface between the openings. In addition, the Gallagher pad can slip beneath the patient, thereby causing discomfort to him or her.

In U.S. Pat. No. 3,431,911 there is shown an absorbent pad having a moisture impermeable layer, a composite absorption layer, and a top layer of liquid permeable foam material which permits passage of liquids to the absorption layer. To prevent pad slippage, the top layer of foam material is folded under the pad and sealed to the surface of the liquid impermeable layer. This arrangement, while functioning to prevent slippage of the pad, actually places a liquid permeable layer on the bottom, and liquid will pass through the liquid permeable foam to the underside of the pad, thereby wetting the sheets, pads, and mattress of the bed, which the liquid impermeable layer is supposed to prevent.

The problem of slippage is addressed also in the device of U.S. Pat. No. 4,536,433 of Sagi et al in which the underside of the moisture impermeable layer is treated with a slip resistant wax, thereby retaining the moisture impermeable characteristics of the bottom layer while preventing slippage of the pad.

All of the prior art devices are designed for specific applications, e.g., floor pad, bed pad, or wheelchair pad, and none of them possess all of the necessary characteristics for use in a variety of applications.

SUMMARY OF THE INVENTION

The present invention is an absorbent pad which may be used as a sanitary pad adjacent toilets or urinals, as a safety pad adjacent stoves or the like where grease and other liquids may be spilled, or as a bed or wheelchair pad for absorption of body fluids from, for example, incontinent patients.

In a preferred embodiment of the invention, the pad comprises a top layer of non-woven polypropylene fabric which is preferably thermoplastic in nature, and which functions as an adsorptive layer for the pad. A second layer, in contact with the underside of the first layer, comprises a cellulosic material which may be cotton, wood or paper pulp, or other absorptive material. A third layer, in contact with the underside of the second layer, comprises a sheet of moisture impermeable material such as polyethylene. Depending upon its projected use, the pad is cut or formed to the desired shape and the edges are sealed as by heat welding, compression or stitching to prevent the escape of moisture contained therein. Where the pad is to be used as a bed or wheelchair pad, it is preferably quilted or embossed by heat and pressure to prevent the absorbent layer from bunching up or shifting.

The underside of the moisture impermeable layer is coated with a thin layer of polyurethane or other suitable foam material which is substantially moisture impermeable. The foam coating gives a highly coefficient of friction in wet or greasy areas and also when in contact with bedsheets, bed pads, seat pads and the like, thereby insuring that the absorbent pad remains in place.

The top, or absorbent layer has pores preferably of no more than 300 microns in diameter, and liquid incident upon the surface is retained in the interstices or pores until it is wicked into the absorbent layer, thereby leaving the entire top surface of the pad substantially dry. When the pad is placed under a urinal, for example, it tends to catch any liquids falling thereon, thereby preventing splashing on the floor, so that a user may place his feet on the floor on either side of the pad and be standing on a clean surface. Because of the foam backing, the pad will not slip. When the pad is used as a bed pad, the adsorptive layer plus wicking action leaves the pad feeling dry to the patient, thereby eliminating the discomfort of a wet surface on which the patient lies. The pad may be made in large blankets, from which are cut the desired sizes and shapes, whose edges are then sealed.

These and other advantages and features of the present invention will be more readily apparent from the following detailed description, read in conjunction with the accompanying drawings, in which:

FIG. 1 is a perspective view of an absorbent pad embodying the principles of the present invention, FIG. 2 is a perspective view of a pad cut to desired shape and quilted; and, FIG. 3 is a cross-sectional view along the line A—A of FIG. 2.

DETAILED DESCRIPTION

Figure 1:
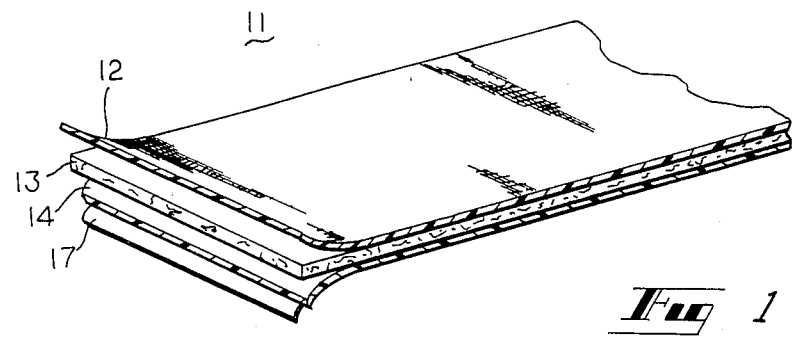
Figure 2:
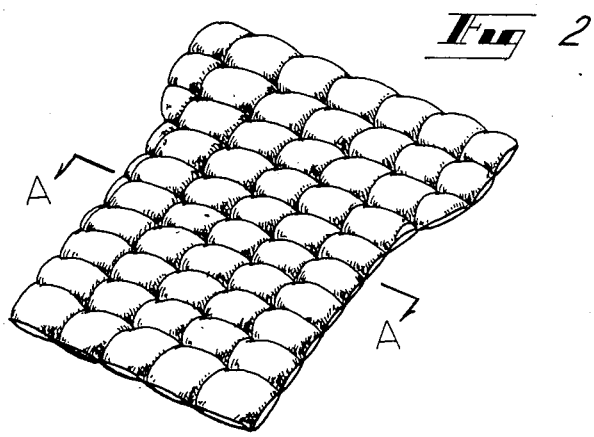

FIG. 1 depicts an absorbent pad 11 embodying the principles of the present invention, and FIG. 2 depicts the pad of FIG. 1 as cut for use, for example, under a suspended urinal, not shown.

Pad 11 is shown in perspective cross-section in FIG. 1 and comprises a top layer 12 of an adsorbent material such as, for example, a non-woven thermoplastic polypropylene material having pores or openings in the range of 200 to 300 microns in diameter or size. Underlying layer 12 is a layer 13 of absorbent material, which may be cotton, wood or paper pulp, or powdered or ground up cellulose material. The pore size in layer 12 is sufficient to permit entry of liquids therein, but small enough to prevent leakage of the material of layer 13 when it is in powdered or granular form. Adsorbent material layer 12 is hydrophobic, but because of the pores, liquid is captured by the material and contained within the pores from which it is wicked or drawn into the absorbent layer 13. The net result is that the top surface of the pad remains substantially dry, thereby minimizing patient discomfort. Where the pad is to be used on the floor, the adsorbent material prevents splashing of liquid falling thereon, thereby maintaining the area adjacent or surrounding the pad free from contaminating liquids. Underlying the absorbent layer 13 is a layer 14 of liquid impermeable material such as a polyethylene, which prevents passage of liquid within the absorbent layer 13 to the exterior of the pad. The bottom surface of layer 14 is coated with a foam layer 17 as will be discussed more fully hereinafter. As can be seen in FIG. 2 the pad 11 has a guilted configuration, which prevents bunching up of the absorbent material. While the quilting is not necessary for a pad intended for use on the floor, it is highly desirable for pads to be used under patients, since bunching of the absorbent material is a common occurrence, and can result in discomfort for the patient.

Figure 3:
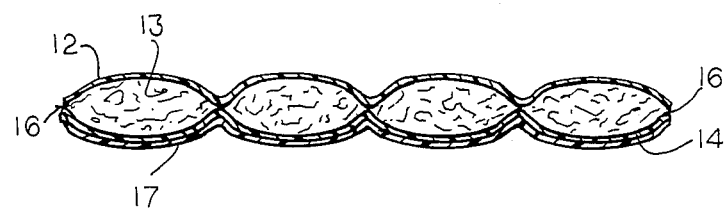

The pad 11 may be quilted in any of a number of ways, such as a pattern of parallel lines or of dots formed by heat and pressure sufficient to deform the layers 12, 13, and 14 and compress them together as shown in FIGS. 2 and 3. As was pointed out heretofore, the basic pad structure may be formed in large sheets and then cut to the desired shape and size. After such cutting, the edges of the pad are joined by heat sealing or by stitching, forming a peripheral seal 16.

The bottom surface of layer 14 is covered with a foam backing 17 of polyurethane, rubber latex, polyethylene, polystyrene or vinyl polymer, which extends along the bottom of the pad within the area defined by the seal 16, and adheres to the under surface of layer 14. The foam may be applied by first applying a low-density liquid polyethylene polymer to the under surface of layer 14, and then spraying the foam material over the polymer after the polymer becomes tacky and then allowing it to cure. It is necessary that foam layer 17 be confined within the limits of seal 16 so that no liquid on or in top layer 12 can be wicked to the underside of the pad.

In use, it has been found that the foam backing of the present invention has greater slip resistance than a wax backing. Thus there is less tendency to slip either on the floor or on the bed. A high slip resistance tends to keep the pad in place, even when used in areas that are inherently greasy, such as around stoves, for example. The pad of the present invention prevents splashing of liquids incident thereon, which it quickly absorbs, leaving a relatively dry top surface. In addition, the pad is a soft, absorbent cushion for patients in bed or in wheelchairs, and the interior layers of the pad do not bunch up, forming uncomfortable lumps.

The foregoing has been illustrative of the principles of the present invention as embodied in a preferred form thereof. Various modifications or alternative forms may occur to workers in the art without departing from the spirit and scope of the invention.

We claim:

1. An absorbent pad comprising a top layer of nonwoven open pored adsorbent material, a second layer of absorbent material underlying said top layer, a third layer of liquid impermeable material underlying said second layer, said top, second and third layers being joined together at their edges to form a peripheral seal, said peripheral seal defining a closed area on the underside of said third layer, and a layer of foam material underlying and adhering to the underside of said third layer solely within said closed area defined by said peripheral seal, and substantially completely covering said area.

2. An absorbent pad as claimed in claim 1 wherein said top layer is formed of a thermoplastic polypropylene material.

3. An absorbent pad as claimed in claim 1 wherein the pores of said adsorbent material are 200 to 300 microns in size.

4. An absorbent pad as claimed in claim 1 wherein the material of said second layer is a cellulose absorbent material.

5. An absorbent pad as claimed in claim 1 wherein said layer of foam material comprises polyurethane foam attached to the underside of said third layer by a coating of low-density polyethylene polymer on the underside of said third layer.

6. An absorbent pad as claimed in claim 1 wherein said pad comprises a plurality of deformed area producing a quilted pattern.

* * * * *